United States Patent [19]
Hamada et al.

[11] Patent Number: 5,863,200
[45] Date of Patent: Jan. 26, 1999

[54] ANGLED DENTAL IMPLANT

[75] Inventors: Michael Osamu Hamada, Playa Delrey, Calif.; Masayuki Takayama, Tokyo, Japan; Norio Kojima, Tokyo, Japan; Kiyoshi Watanabe, Tokyo, Japan; Yoshimasa Akaishi, Tokyo, Japan

[73] Assignee: GC Corporation, Tokyo, Japan

[21] Appl. No.: 908,161

[22] Filed: Aug. 7, 1997

[30] Foreign Application Priority Data

Aug. 9, 1996 [JP] Japan .................................. 8-226157
Jun. 27, 1997 [JP] Japan .................................. 9-185977

[51] Int. Cl.⁶ .................................................. A61C 8/00
[52] U.S. Cl. ............................................................ 433/173
[58] Field of Search ................................... 433/172, 173, 433/174

Primary Examiner—Nicholas D. Lucchesi
Attorney, Agent, or Firm—Oblon, Spivak, McClelland, Maier & Neustadt, P.C.

[57] ABSTRACT

An angled dental implant includes an implant fixture to be implanted into a hole formed in the mandible of the patient, an abutment having a truncated conical portion configured to be bolted to the fixture, a cylinder configured to engage the abutment, where the cylinder has a center line that is inclined relative to a longitudinal axis of the fixture, wherein the cylinder is fastened to the abutment with a bolt aligned with the center line of the cylinder.

12 Claims, 8 Drawing Sheets

ANGLED DENTAL IMPLANT

FIELD OF THE INVENTION

The present invention relates to an angled dental implant comprising an implant fixture which is implanted in and fixed to an implantation hole formed in a mandible of the deficit tooth portion and a dental prosthesis retainer which is connected and fixed to the implant fixture, without failure in the esthetics by parts other than the dental prosthesis in case where it is placed in the oral cavity.

BACKGROUND OF THE INVENTION

Hither to, as the prosthetic method in a deficit tooth portion, a method for using a bridge and a method for using a denture base have been generally employed.

However, since the method for using a bridge is a method in which healthy natural teeth in the both sides of the deficit tooth portion are cut to prepare an abutment tooth, with which is then engaged a metallic body provided in a dental prosthesis positioned in the deficit tooth portion, it had such defects that not only the healthy natural teeth must be cut to provide an engaging portion, but also since an occlusion pressure is not directly applied to the dental prosthesis part positioned in the deficit tooth portion, a bone loss is likely caused in the instant site.

Also, the method for using a denture base is a method in which a denture is fixed to a denture base made of a synthetic resin or the like to prepare a dental prosthesis. According to this method, the occlusal force which acts to the dental prosthesis is burdened by the remaining natural teeth and/or the oral mucosa, and therefore, this method involved such defects that a sense of incongruity is generated during the use of the dental prosthesis and that the matter wherein the dental base covers receptors of the taste lying scattered in the oral mucosa tissue, thereby generating blunting of the taste. In addition, it involved a serious defect that a loss of the residual ridge is caused during the use for a long period of time.

Thus, as a therapeutic method for overcoming these defects, a technology of dental implant in which an implant fixture acting as a retention balancer of a dental prosthesis is implanted in an implantation hole formed in a mandible of the deficit tooth portion and made act for the functions of a tooth root in a natural tooth, and a fixture is connected and fixed to the implant fixture in the oral cavity side thereof, whereby a dental prosthesis is fixed to this fixture of a dental prosthesis was developed and has been being exploited.

When a therapeutic method for using such a dental implant is exploited, the dental prosthesis can be fixed without covering the oral mucosa. Therefore, this method has such advantages that neither a sense of incongruity nor blunting of the taste is generated at the time when the dental prosthesis is installed, a use feeling like natural teeth is obtained, and that since a proper occlusal force is imparted to the mandible, the bone loss to be highly expected in case where no implant fixture is implanted can be suppressed at the minimum. Thus, this therapeutic method has rapidly developed to such an extent that it can be applied to not only the case where a single tooth is lost, or two or more teeth are locally lost but also the case of an edentulous jaw (i.e., all teeth are lost).

According to the therapeutic method for using such a dental implant, in order that an implantation hole in which an implant fixture is implanted is formed in a mandible of the deficit tooth portion and that after the implant fixture is implanted in this implantation hole, a screw hole exposing in the center in the oral cavity side of the implanted implant fixture is clogged, and at the same time, it is inhibited that the bone grows to the oral cavity side over the implant fixture during the healing stage, there is mainly employed a double technique in which in the oral cavity side of the implant fixture, a cover screw formed such that the end portion thereof in the implant fixture side has a size equal to or larger than that of the end portion of the implant fixture in the oral cavity side, while the oral cavity side thereof has a size larger than that of the end portion in the implant fixture side is screwed in the aforesaid screw hole; a gingiva surrounding the implantation hole is sutured; after not only the implanted implant fixture is thoroughly connected to the mandible of the deficit tooth portion, but also the operated portion where the implantation hole has been formed is healed, the gingiva portion in the oral cavity side having the implant fixture implanted therein is again cut to take apart the cover screw from the implant fixture; in the oral cavity side portion of the implant fixture, a healing abutment in which the outer size thereof in the implant fixture side is equal to that of the end portion of the implant fixture in the oral cavity side, while the length thereof is longer than the thickness of the surrounding gingiva is screwed; and after the cut surrounding gingiva portion has been healed, a fixing device of a dental prosthesis is connected and fixed thereto.

In this double technique, after the surrounding gingiva portion cut in order to screw the healing abutment has been healed; the healing abutment is taken apart from the implant fixture; an abutment having a gold cylinder external engagement portion, which functions as a support for connecting and fixing a fixing device of a dental prosthesis, is connected and fixed to the oral cavity portion of the implant fixture by screwing an abutment screw through which the abutment is penetrated in the aforesaid screw hole; and then, impression taking for preparing a dental prosthesis is carried out. In this case, the gold cylinder external engagement portion provided in the portion of the abutment nearest the oral cavity includes a case that as in posterior tooth portions, it is connected and fixed such that its center line is coincident with the center axis of the implant fixture and a case that as in maxillary anterior tooth portions, its center line is inclined against the center axis of the implant fixture. In any cases, the gold cylinder external engagement portion is connected and fixed so as to enable to fix the position against the implant fixture.

In such dental implant technique, in order to prepare dental prostheses having a good appearance, it is very important to select a construction for each of the abutment having a gold cylinder external engagement portion functioning as a support for connecting and fixing the fixing device of a dental prosthesis and the gold cylinder to be externally engaged in the gold cylinder external engagement portion of the abutment.

That is, in the abutment, a portion in which the end portion thereof in the implant fixture side has a size equal to that of the end portion of the implant fixture in the oral cavity side, while the oral cavity side has a size larger than that of the end portion in the implant fixture side is provided in the implant fixture side, and in the oral cavity side of the portion provided in the implant fixture side, the gold cylinder external engagement portion functioning as a fixing device of a dental prosthesis must be provided. In particular, in order to enable to apply to cases of maxillary anterior tooth portions or cases where an implant fixture as an artificial tooth root portion is not implanted in a mandible of the deficit tooth portion with a right angle, an abutment in which the axial line of the gold cylinder external engagement portion is inclined with an angle against the axial line of the implant fixture has been recently prepared.

In addition, the gold cylinder functioning as the fixing device of a dental prosthesis must be formed such that the end portion thereof in the implant fixture side has the same size as in the end portion in the oral cavity side functioning as a base end portion of the gold cylinder external engagement portion of the abutment. In particular, in case of the gold cylinder as described above, in which the axial line of the gold cylinder external engagement portion is inclined with an angle against the axial line of the implant fixture, it is of a problem how the gold cylinder is externally engaged in the gold cylinder external engagement portion of the abutment.

Hitherto, as the construction for the abutment and the gold cylinder in which the axial line of the gold cylinder functioning as the fixing device of a dental prosthesis is inclined with an angle against the axial line of the implant fixture implanted in the mandible of the deficit tooth portion, there has been proposed a construction in which as disclosed in, for example, JP-A-1-190350, an abutment is provided in the oral cavity side thereof a portion becoming in a cylindrical form having the same diameter after forming such that the end portion thereof in the implant fixture side has the same size as in the end portion of the implant fixture in the oral cavity side, while the oral cavity side thereof has a size larger than that in the end portion in the implant fixture side; in the oral cavity side of the portion becoming in a cylindrical form provided in the oral cavity side, the end surface in the oral cavity side of the expansion portion provided in the state of being further expanded from the aforesaid portion has a plane inclined against the axial line of the implant fixture in the surrounding thereof; in a portion in the center side of the inclined plane and positioned nearest the oral cavity side, a gold cylinder external engagement portion whose center line is inclined against the center axis of the implant fixture is provide; the truncated conical gold cylinder functioning as the fixing device of a dental prosthesis comes into contact with the aforesaid plane in the state that the end surface thereof in the implant fixture side is inclined against the axial line of the implant fixture.

Figure 14:
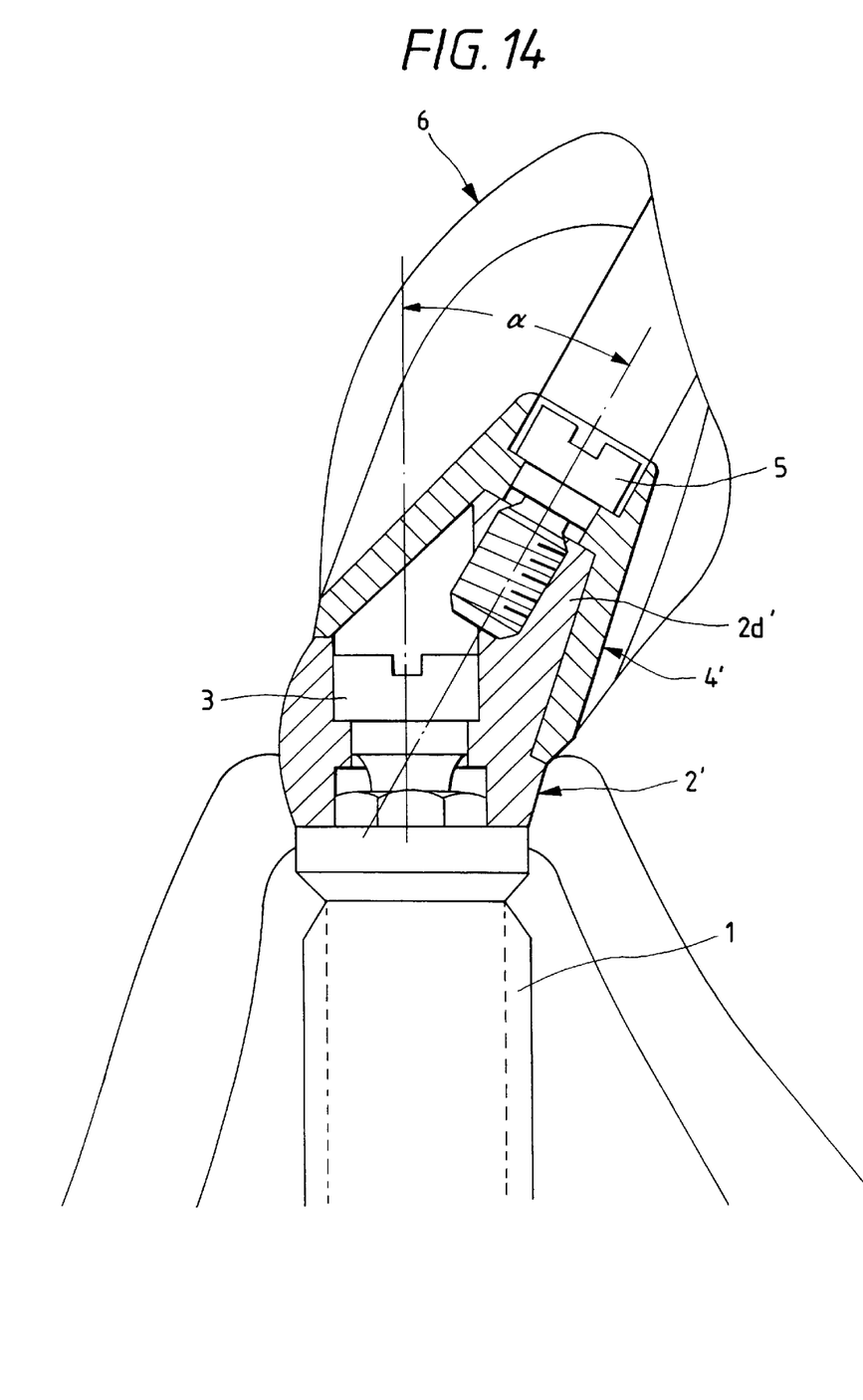
FIG. 14 is a cross-sectional explanatory view of one embodiment in a state that the therapy is completed with a gold cylinder having a dental prosthesis formed thereon using a conventional angled dental implant being fixed.

However, in the state that the therapy by means of a dental implant using the abutment and gold cylinder in the above-described conventional example has been completed, as in a anterior tooth portion shown in FIG. 14, an abutment 2* is connected and fixed to an implant fixture 1 by means of an abutment screw 3 while inclining the center line of a gold cylinder external engagement portion 2d* with an angle (against the center axis of the implant fixture 1, and in the oral cavity side of the abutment 2* as well as of the abutment screw 3, a gold cylinder 4* functioning as a fixing device of a dental prosthesis 6 is connected and fixed to the abutment 2* by means of a gold screw 5. In this case, the dental prosthesis 6 is fixed only in the surrounding of the gold cylinder 4*, and if an external surface of an end portion of the dental prosthesis 6 in the side of the implant fixture 1 is larger than an end surface of the abutment 2* in the oral cavity side, bacteria likely retain in this discontinuous surface portion to cause an inflammation in the gingiva. Accordingly, since the dental prosthesis 6 is provided only in the oral cavity side more inside than the end portion of the gold cylinder 4* in the implant fixture 1 side, having the same shape as the end surface of the abutment 2* in the oral cavity side, both the expansion portion of the abutment 2* and the end portion of the gold cylinder 4* in the implant fixture 1 side are exposed, leading to a defect such that the esthetics are remarkably deteriorated.

In addition, as an angled dental implant which is freed from the foregoing defect, there has also been proposed one having a structure comprising a truncated conical portion in which in the above-described conventional abutment, the end portion in the implant fixture side has the same size as the end portion of the implant fixture in the oral cavity side, and the oral cavity side is larger than the end portion in the implant fixture side; and not only in the oral cavity side of this truncated conical portion, an external periphery side plane perpendicular against the axis of the truncated conical portion is provided, but also in a portion positioned in the center side of the truncated conical portion and nearest the oral cavity side, a dental prosthesis retaining portion whose center line is inclined against the center axis of the implant fixture is provided.

However, since this angled dental implant does not use a gold cylinder, a dental prosthesis having such a shape that the end portion in the implant fixture side comes into contact with the above-described external periphery side plane of the abutment and that the dental prosthesis is retained in the dental prosthesis retaining portion of the abutment must be prepared. In addition, since in the portion of this dental prosthesis to be retained in the dental prosthesis retaining portion of the abutment, a bolt hole must be provided in the state that it penetrates from the inclined external surface of the dental prosthesis retaining portion through the center of the truncated conical portion in order to penetrate an abutment screw for connecting and fixing the abutment to the implant fixture, the dental prosthesis must be prepared in such a manner that the presence of this bolt hole does not mind. Accordingly, in order to prepare a dental prosthesis with high precision, this case not only needs many steps as compared with the case where the gold cylinder is used, but also involves a fatal defect that it is difficult to achieve the preparation with high precision.

SUMMARY OF THE INVENTION

An object of the present invention is to overcome the defects of the conventional techniques as described above and to provide an angled dental implant by using a gold cylinder, which can be prepared with good esthetics and high precision in case where it is fixed to a dental prosthesis.

The present inventors made extensive and intensive investigations in order to dissolve the above-described problems. As a result, it has been found that in the above-described conventional angled dental implant using a gold cylinder, not only since the plane of the abutment provided in the oral cavity side which comes into contact with the end surface of the gold cylinder in the implant fixture side is provided in the surrounding of the expansion portion projected from the top portion of the gingiva in the oral cavity side to the oral cavity side, the esthetics are lowered because this expansion portion is exposed in a color tone different from that of conventional dental prostheses in which the expansion portion is covered by a porcelain, but also since the external shape of the end portion of the gold cylinder to which a dental prosthesis is fixed in the implant fixture side is immediately expanded from the external shape of the plane of the above-described abutment in the oral cavity side which comes into contact with the end surface of the gold cylinder provided in the implant fixture side and then reduced in diameter, it is impossible to fix a dental prosthesis which is usually covered by a porcelain to the external surface end portion of the gold cylinder in the implant fixture side and hence, the abutment and the gold cylinder each of which is different in color tone from the dental prosthesis are exposed from the gingiva portion to the oral cavity side, leading to a reduction in the esthetics.

Thus, the present inventors made extensive and intensive investigations in order to provide an abutment of an angled dental implant with good esthetics. As a result, it has been found that the above-described problems can be dissolved by the construction of the angled dental implant as described below.

That is, the present invention relates to an angled dental implant comprising a structure in which:

an angular pipe portion in the oral cavity side of an implant fixture to be implanted in and fixed to an implantation hole formed in a mandible of the deficit tooth portion is engaged in an angular pipe concave portion provided in the side of the implant fixture of an abutment;

- the abutment comprises a truncated conical portion in which an end portion thereof has an outer diameter the same as that of an end of an approximate column of the implant fixture, the outer diameter increases as it becomes far from the implant fixture, and the oral cavity side thereof has such a height that it is positioned in the side of the implant fixture as compared with a top portion in the oral cavity side of a mandible of a patient; in the oral cavity side of the truncated conical portion, an external periphery side plane perpendicular against the axis of the truncated conical portion; in a portion positioned in the center side of the truncated conical portion and in the oral cavity side, a gold cylinder external engagement portion whose center line is inclined against the center axis of the implant fixture is provided; and a bolt hole is provided in such a manner that it penetrates from the inclined external surface of the gold cylinder external engagement portion to the center of the truncated conical portion, with a female screw being provided in the oral cavity side of the gold cylinder external engagement portion;
- the abutment is connected and fixed by means of an abutment screw to be screwed in a female screw of the implant fixture while penetrating the bolt hole of the abutment and further through the angular pipe portion of the implant fixture;
- the external periphery side plane of the abutment is brought into contact with a plane of an end surface in the side of the implant fixture; and the oral cavity side thereof is in an external shape whose diameter is reduced as compared with the plane;
- an engagement portion provided in a space of a gold cylinder forming a cast piece anchorage whose center line is coincident with the center line of the gold cylinder external engagement portion of the abutment inclined against the center axis of the implant fixture is externally engaged in the gold cylinder external engagement portion; and
- the gold cylinder is connected and fixed to the abutment by means of a gold screw to be screwed with a female screw provided in the oral cavity side of the gold cylinder external engagement portion of the abutment while penetrating through a bolt hole provided in a penetration state in the oral cavity side of the gold cylinder.

And, in such construction, it has become clear by the present invention that:

- If an angular pipe portion is provided in the side of the implant fixture of the gold cylinder external engagement portion of the abutment, and an angular pipe concave portion to be engaged in the foregoing angular pipe portion in the side of the implant fixture in a space of the gold cylinder is provided, in case where the dental implant is used for a single tooth, the gold cylinder can be accurately connected and fixed to the gold cylinder external engagement portion of the abutment without occurrence of any revolution;
- If the abutment comprises a construction comprising a first member comprising the truncated conical portion in which in the oral cavity side, a groove concaved in the side of the implant fixture and/or a projection projected in the oral cavity side are formed in the inside of the external periphery side plane; and a second member in which in the side of the implant fixture, a convex to be internally engaged in the foregoing groove and/or a concave to be externally engaged in the foregoing projection are provided, the position is fixed in a state that the groove and convex and/or the projection and concave are engaged in each other, and in a portion positioned in the oral cavity side, the gold cylinder external engagement portion whose center line is inclined against the center axis of the implant fixture, since the construction is one comprising the first member comprising a truncated conical portion in a linear symmetry or approximately linear symmetry state with respect to its center line and the second member provided with the gold cylinder external engagement portion in an approximately linear symmetry state with respect to its center line, not only its preparation is easy, but also it is possible to prepare the second member by casting; and further, the external periphery surface of the truncated conical portion of the first member functioning as a portion coming into contact with a gingiva can be mechanically processed so as to have a fine plane roughness, whereby the sealability by the gingiva is improved to prevent bacteria from retention; and
- If a collar portion partitioning a base end portion of a dental prosthesis, which is formed in a thin thickness in the side of the implant fixture and has a step portion in the oral cavity side, is provided, the position of the base end portion to be fixed to the external periphery of the gold cylinder can be made accurate, and the appearance can be further improved.

DETAILED DESCRIPTION OF THE PREFERRED EMBODIMENTS

Preferred embodiments of the abutment of the angled dental implant according to the present invention will be described hereunder in more detail with reference to the accompanying drawings.

Figure 1:
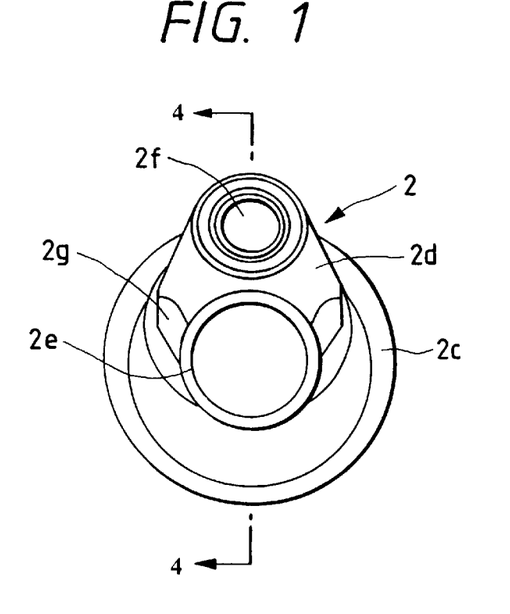
FIG. 1 is a planar view of one embodiment of an abutment used in an angled dental implant according to the present invention.
Figure 2:
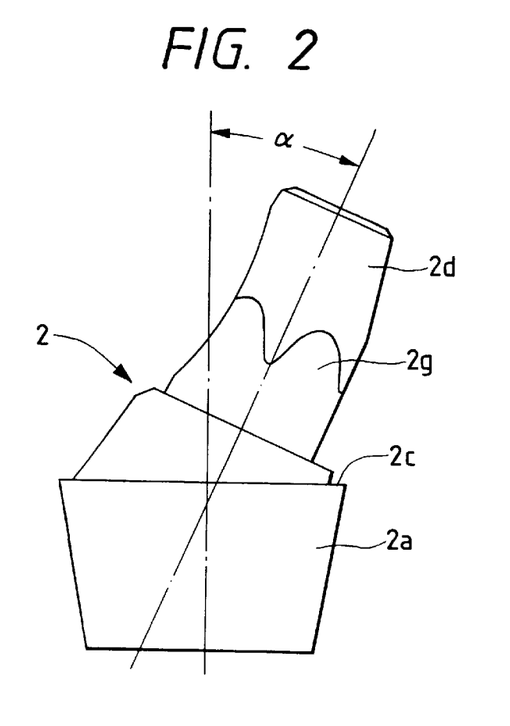
FIG. 2 is a right-side view of the abutment as shown in FIG. 1.
Figure 3:
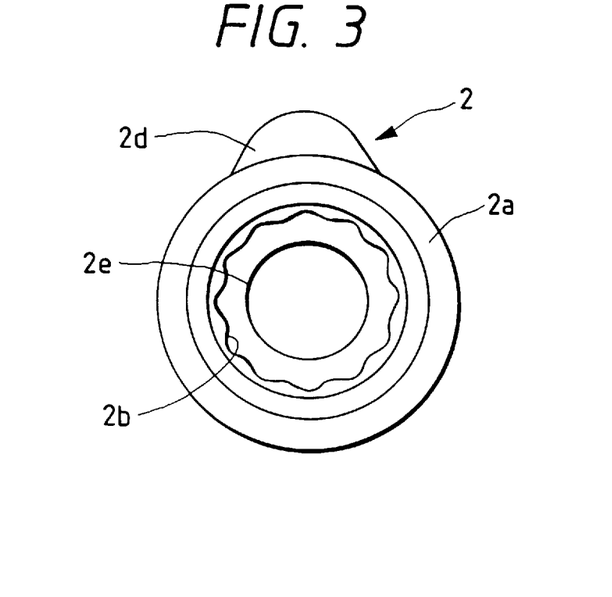
FIG. 3 is a bottom view of the abutment as shown in FIG. 1.
Figure 4:
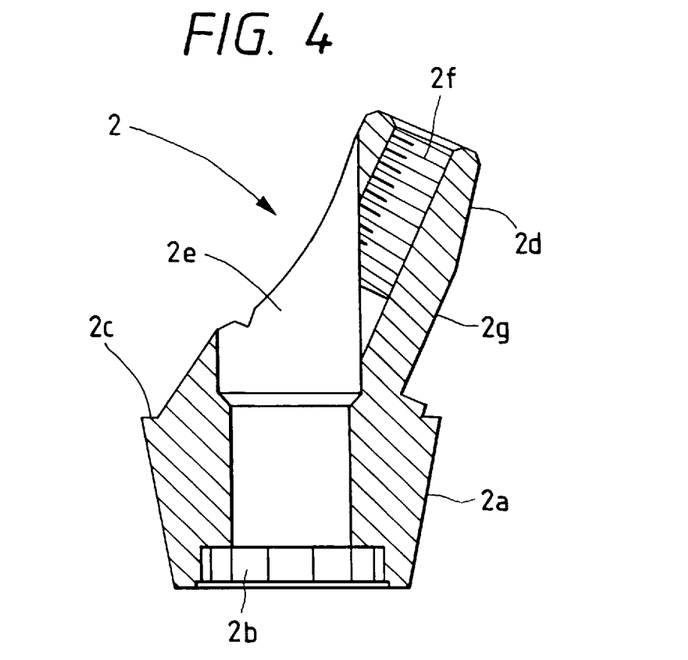
FIG. 4 is an A—A line cross-sectional view in FIG. 1.
Figure 5:
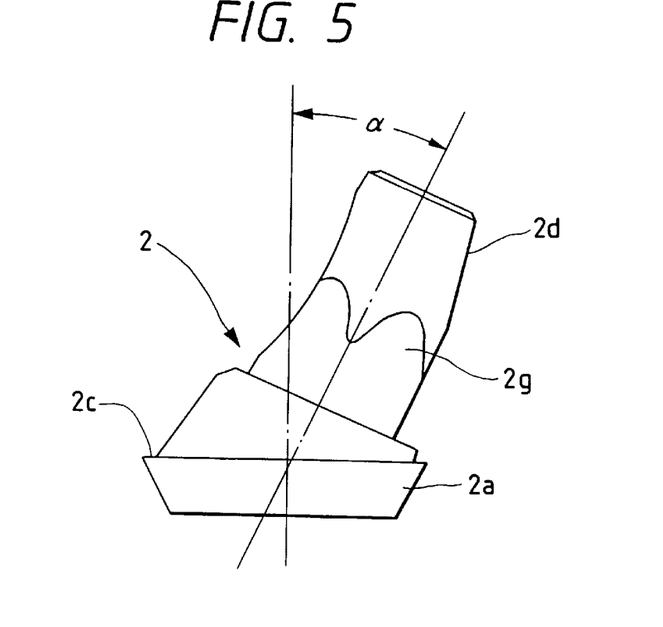
FIG. 5 is a right-side view of another embodiment of an abutment used in an angled dental implant according to the present invention, in which the height of a truncated conical portion is lower than that in the abutment of the embodiment as shown in FIG. 1.
Figure 6:
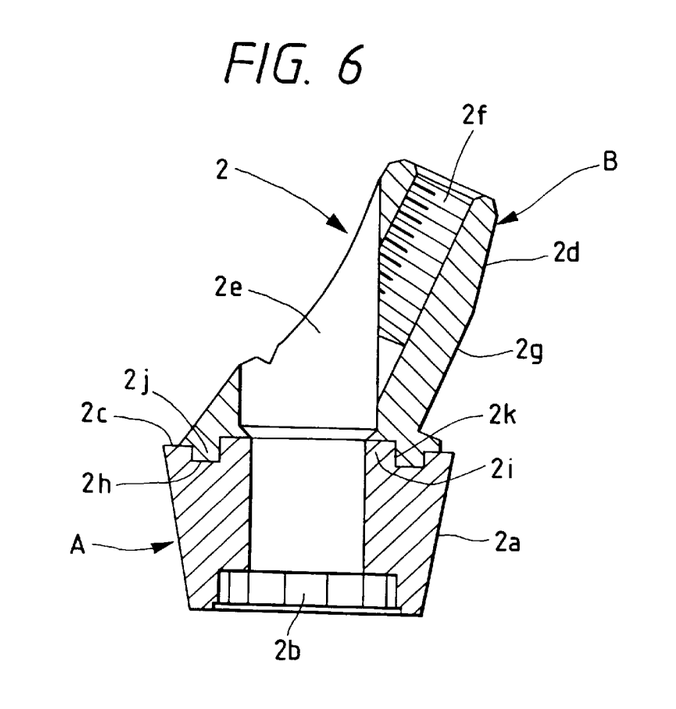
FIG. 6 is a cross-sectional view of an embodiment of an abutment used in an angled dental implant according to the present invention, which comprises a first member and a second member, corresponding FIG. 4.
Figure 7:
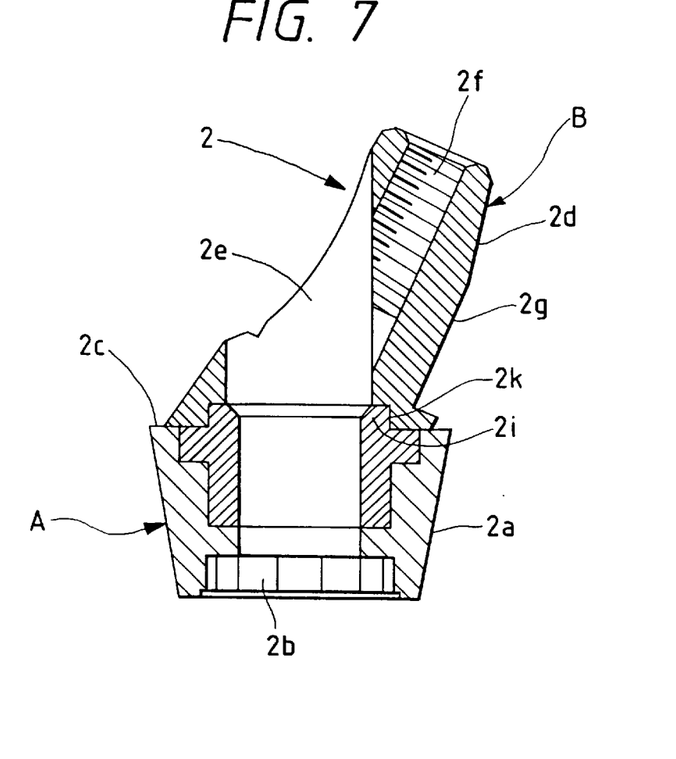
FIG. 7 is a cross-sectional view of an embodiment of an abutment used in an angled dental implant according to the present invention, in which the first member comprises two members, corresponding to FIG. 4.
Figure 8:
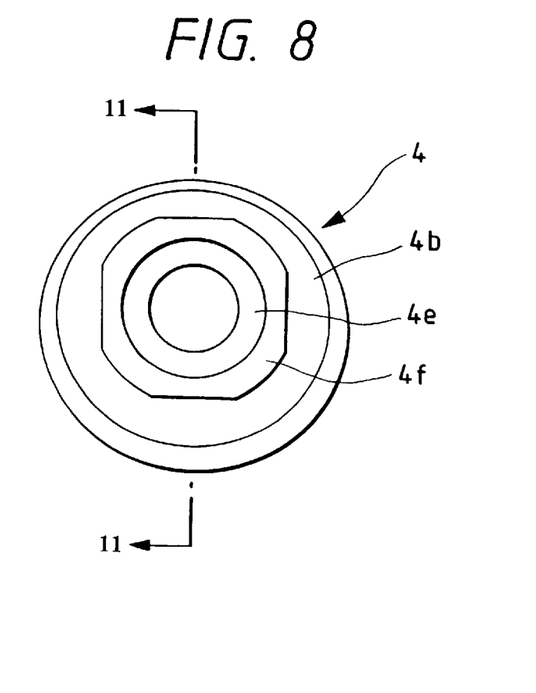
FIG. 8 is a planar view of one embodiment of a gold cylinder used in an angled dental implant according to the present invention.
Figure 9:
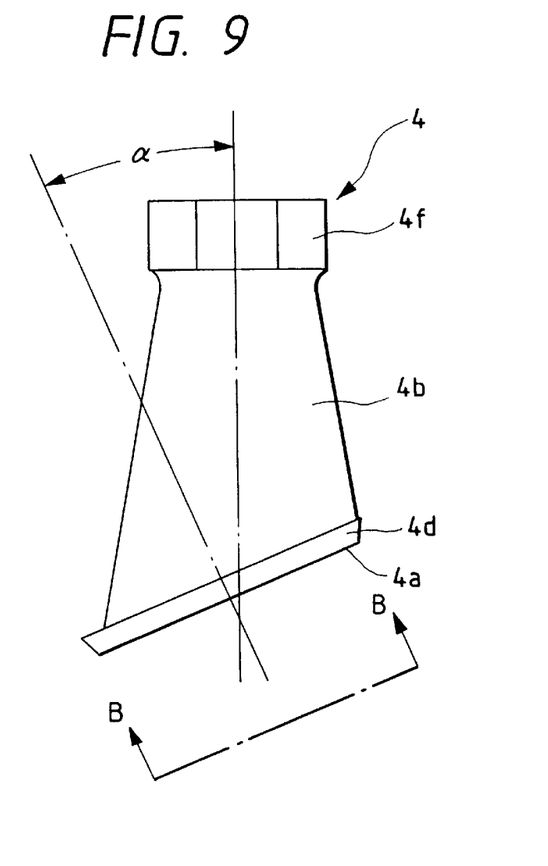
FIG. 9 is a right-side view of the gold cylinder as shown in FIG. 8.
Figure 10:
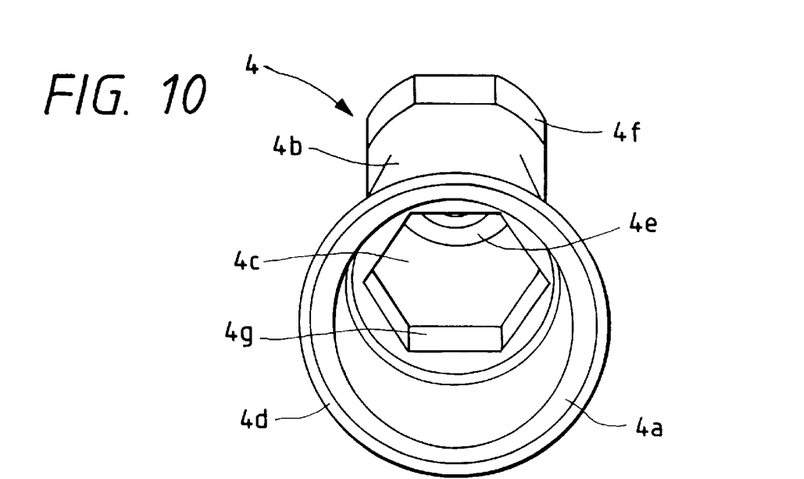
FIG. 10 is a B—B line view in FIG. 9.
Figure 11:
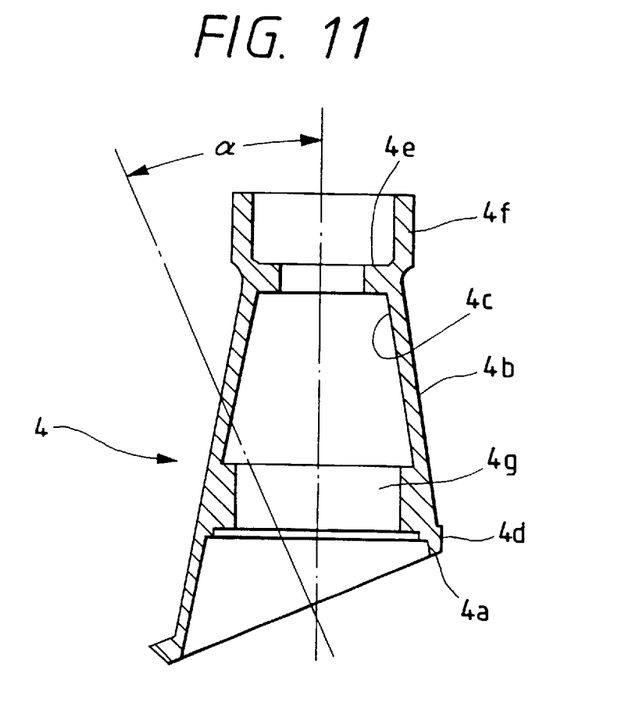
FIG. 11 is a C—C line cross-sectional view in FIG. 8.
Figure 12:
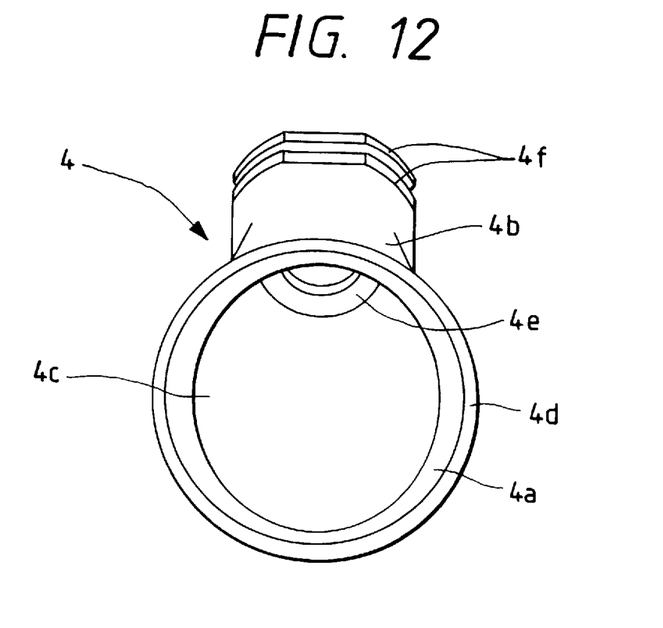
FIG. 12 is a view of another embodiment in which in an implant fixture side of an inner space portion of the gold cylinder of the embodiment as shown in FIG. 8, no angular pipe concave portion to be engaged in an angular pipe portion provided in an implant fixture side of a gold cylinder external engagement portion of an abutment is provided, corresponding to FIG. 10.
Figure 13:
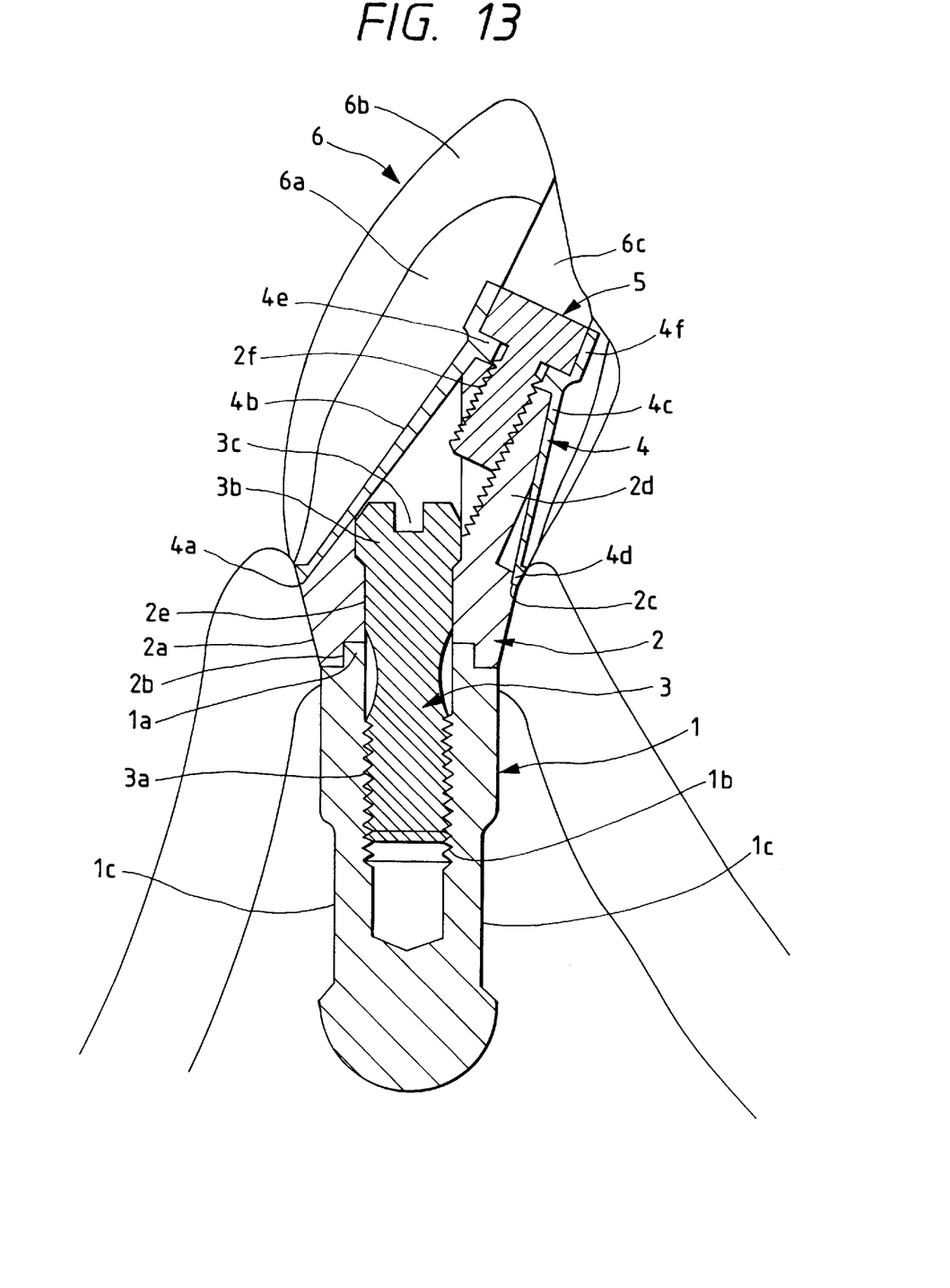
FIG. 13 is a cross-sectional explanatory view of one embodiment in a state that the therapy is completed with a gold cylinder having a dental prosthesis formed thereon by using an angled dental implant according to the present invention being fixed.

FIG. 1 is a planar view of one embodiment of an abutment used in an angled dental implant according to the present invention;

FIG. 2 is a right-side view of the abutment as shown in FIG. 1;

FIG. 3 is a bottom view of the abutment as shown in FIG. 1;

FIG. 4 is an A—A line cross-sectional view in FIG. 1;

FIG. 5 is a right-side view of another embodiment of an abutment used in an angled dental implant according to the present invention, in which the height of a truncated conical portion is lower than that in the abutment of the embodiment as shown in FIG. 1;

FIG. 6 is a cross-sectional view of an embodiment of an abutment used in an angled dental implant according to the present invention, which comprises a first member and a second member, corresponding FIG. 4;

FIG. 7 is a cross-sectional view of an embodiment of an abutment used in an angled dental implant according to the present invention, in which the first member comprises two members, corresponding to FIG. 4;

FIG. 8 is a planar view of one embodiment of a gold cylinder used in an angled dental implant according to the present invention;

FIG. 9 is a right-side view of the gold cylinder as shown in FIG. 8;

FIG. 10 is a B—B line view in FIG. 9;

FIG. 11 is a C—C line cross-sectional view in FIG. 8;

FIG. 12 is a view of another embodiment in which in an implant fixture side of an inner space portion of the gold cylinder of the embodiment as shown in FIG. 8, no angular pipe concave portion to be engaged in an angular pipe portion provided in an implant fixture side of a gold cylinder external engagement portion of an abutment is provided, corresponding to FIG. 10; and FIG. 13 is a cross-sectional explanatory view of one embodiment in a state that the therapy is completed with a gold cylinder having a dental prosthesis formed thereon by using an angled dental implant according to the present invention being fixed.

First of all, the construction of the dental implant is explained by using FIG. 13.

A numeral 1 is an implant fixture made of titanium having good affinity with living bodies, which is implanted in and fixed to an implantation hole formed in a mandible of the deficit tooth portion. In the embodiment shown here, the point to be implanted in the mandible is in an approximate hemisphere form; and a succeeding portion is in an approximate column form in which an engagement portion 1c in a concave groove form to be engaged in the mandible is provided in a predetermined potion of the surrounding thereof; an angular pipe portion 1a in a form of, e.g., a hexagon is provided in a center portion of an end portion in the oral cavity side of the approximate column portion; and a female screw 1b penetrating through the angular pipe portion 1a and coming into the above-described approximate column portion is provided. Implant fixtures not having such a structure are also applicable to the angled dental implant according to the present invention.

A numeral 2 is an abutment functioning as a support, which is connected and fixed to the implant fixture 1 in the oral cavity side and to which a gold cylinder 4 functioning as a fixing device of a dental prosthesis 6 as described below is connected and fixed. The abutment comprises a truncated conical portion 2a in which an end portion thereof in the side of the implant fixture 1 has an outer diameter the same as that of an end of the approximate column of the implant fixture 1. The outer diameter of portion 2a increases as it becomes distal from the implant fixture 1, and the oral cavity side thereof has such a height that it is positioned in the side of the implant fixture 1 as compared with a top portion in the oral cavity side of a mandible of a patient. The truncated conical portion 2a is preferably made of titanium or ceramics having good affinity with living bodies because it is a site coming into contact with the mandible. Also, in the side of the implant fixture 1, the abutment 2 is provided with an angular pipe concave portion 2b (for example, in case where the angular pipe portion 1a of the implant fixture 1 is hexagonal, the angular pipe concave portion 2b is a hexagonal or dodecagonal concave portion) to be engaged in the above-described angular pipe portion 1a of the implant fixture 1. In the oral cavity side of the truncated conical portion 2a, the abutment 2 is provided with an external periphery side plane 2c perpendicular against the axis of the truncated conical portion 2a, with which the end surface of the gold cylinder in the side of the implant fixture 1 comes into contact. In a portion positioned in the center side of the truncated conical portion 2a and in the oral cavity side, a gold cylinder external engagement portion 2d whose center line is inclined with a predetermined angle (against the center axis of the implant fixture 1 is provided) and a bolt hole 2e is provided in such a manner that it penetrates from the inclined external surface of the gold cylinder external engagement portion 2d to the center of the truncated conical portion 2a, with a female screw 2f being provided in the oral cavity side of the gold cylinder external engagement portion 2d. In the side of the implant fixture 1 of the gold cylinder external engagement portion 2d, an angular pipe portion (for example, a hexagonal pipe portion) 2g to be engaged in the angular pipe portion 1a of the implant fixture 1 as shown in FIGS. 1 to 7 is provided. Alternatively, as shown in FIG. 13, no angular pipe portion is provided, but it is merely in a truncated conical form.

The abutment 2, as shown in FIGS. 6 and 7, comprises a first member A comprising the truncated conical portion 2a in which a concave groove 2h in the side of the implant fixture 1 and/or a projection 2i projected in the oral cavity side are formed in the inside of the external periphery side plane 2c. A and a second member B in which a projection 2j to be internally engaged in the groove 2h and/or a groove 2k to be externally engaged in the projection 2i are provided. The position is fixed in a state that the groove 2h and projection 2j and/or the projection 2i and groove 2k are engaged in each other. In a portion positioned in the oral cavity side, the gold cylinder external engagement portion 2d whose center line is inclined against the center axis of the implant fixture 1 can be employed. According to this construction, not only the construction can be made from members of a linear symmetry or an approximately linear symmetry against the respective center lines (the center line of the truncated conical portion 2a in the case of the first member A; and the center line of the gold cylinder external engagement portion 2d of the second member B), so that its preparation is easy, but also in particular, the external periphery surface of the truncated conical portion 2a of the first member A functioning as a portion coming into contact with a gingiva can be mechanically processed so as to have a fine plane roughness, whereby the sealability by the gingiva is improved to prevent bacteria from retention. Thus, this construction is preferable.

And, each of the first member A and the second member B can also be constructed from two or more members which are engaged in each other and position-fixed, as shown in FIG. 7 in which, however, only the first member A is explained.

As the abutment since the thickness of the gingiva is different depending upon patients, two types having a varied height of the truncated conical portion 2a of, e.g., 1 mm, 2 mm, and 3 mm are prepared.

Referring again to FIG. 13, a slot 3c is formed in a top portion of an abutment screw 3 for connecting and fixing the abutment 2 in the oral cavity side of the implant fixture 1. Following this top portion, a stopper portion 3b coming into contact with the end surface in the oral cavity side of the bolt hole 2e of the abutment 2 is provided; and a male screw 3a which is screwed in the female screw 1b of the implant fixture while penetrating through the bolt hole 2e of the abutment 2 as well as the angular pipe portion 1a of the implant fixture 1 is provided.

Cylinder 4 is made of a noble metal-based alloy such as gold and is configured to be connected and fixed to the abutment 2 by means of a screw 5 which is received by the female screw 2f provided in cylinder external engagement portion 2d in the oral cavity side of the abutment 2 connected and fixed to the oral cavity side of the implant fixture 1 by means of the abutment screw 3. In the side of the implant fixture 1, a plane 4a forming the end surface in the side of the implant fixture 1, which comes into contact with the external periphery side plane 2c perpendicular the axis of the truncated conical portion 2a of the abutment 2 is provided. The oral cavity side thereof is in a predetermined external shape whose diameter is reduced as compared with the plane 4a and forms a cast piece anchorage 4b of the dental prosthesis 6 whose center line is coincident with the center line of the gold cylinder external engagement portion 2d inclined with a predetermined angle (against the center axis of the implant fixture). The internal portion of cylinder 4 has a space which can receive a top portion of the abutment screw 3 and the gold cylinder external engagement portion 2d of the abutment 2, and in this space, an external engagement portion 4c to be externally engaged in the gold cylinder external engagement portion 2d of the abutment 2. In the oral cavity side, a projected portion 4e into which the top portion of the gold screw 5 is implanted and then supported is formed. In the external surface of the cast piece anchorage 4b nearest the oral cavity side, a top portion 4f whose external shape is made large in order to prevent a cast piece 6a of the dental prosthesis 6 as described below from getting out of place from the cast piece anchorage 4b; and in this top portion 4f, a planar portion is provided for preventing the cast piece 6a of the dental prosthesis 6 from revolving around the cast piece anchorage 4b, as well as for other purposes. If an angular pipe concave portion 4g to be engaged in the angular pipe portion 2g provided in the side of implant fixture 1 of the gold cylinder external engagement portion 2d of the abutment 2 is provided in the side of the implant fixture 1 of the above-described space, in case where the dental implant is used for a single tooth, the gold cylinder 4 can be accurately connected and fixed to the gold cylinder external engagement portion 2d of the abutment 2 without occurrence of any revolution. And, it is preferable that a collar portion 4d partitioning the base end portion of the dental prosthesis 6, which is formed in a thin thickness in the side of the implant fixture 1 and has a step portion in the oral cavity side, is provided.

A numeral 6 is a dental prosthesis comprising a cast piece 6a cast in a state that it is anchored in the external periphery of the cast piece anchorage 4b of the gold cylinder 4 and a porcelain 6b formed in the external periphery of the cast piece 6a, in which in the extended portion of the center line of the cast piece anchorage 4b, a hole 6c having a size such that the top portion of the gold screw 5 can pass therethrough is provided; and this hole 6c is clogged by a dental cement or the like after the gold cylinder 4 having the dental prosthesis 6 fixed thereto is connected and fixed to the abutment 2 by means of the female screw 2f screwed in the oral cavity side of the abutment 2. If this dental prosthesis 6 is provided with the collar portion 4d partitioning the base end portion of the dental prosthesis, which is formed in a thin thickness in the side of the implant fixture 1 and has a step portion in the oral cavity side, the position of the base end portion to be fixed to the external periphery of the gold cylinder 4 can be made accurate, and the appearance can be further improved.

In order to undergo the therapy by using the angled dental implant having the above-described structure according to the present invention, the abutment 2 having the truncated conical portion 2a having a height suited to the thickness of the gingiva of a patient is first selected.

Then, the angular pipe concave portion 2b provided in the side of the implant fixture 1 of the truncated conical portion 2a of the selected abutment 2 is engaged in the angular pipe portion 1a in the oral cavity side of the implant fixture 1 which has become in a state such that it is implanted in the implantation hole formed in the mandible of the deficit tooth portion and can function in place of the tooth root of a natural tooth; and in a portion in the center side of the truncated conical portion 2a and nearest the oral cavity side, the center axis of the gold cylinder external engagement portion 2d provided in such a manner that the center line thereof is inclined with an angle (against the center axis of the implant fixture 1 is made towards a predetermined direction in the oral cavity side. At this time, in case where the abutment 2 comprises the first member A comprising the truncated conical portion 2a in which in the oral cavity side, the groove 2h concaved in the side of the implant fixture 1 and/or the projection 2i projected in the oral cavity side are formed in the inside of the external periphery side plane 2c; and the second member B in which in the side of the implant fixture 1, the convex 2j to be internally engaged in the groove 2h and/or the concave 2k to be externally engaged in the projection 2i are provided, the position is fixed in a state that the groove 2h and convex 2j and/or the projection 2i and concave 2k are engaged in each other, and in a portion positioned in the oral cavity side, the gold cylinder external engagement portion 2d whose center line is inclined against the center axis of the implant fixture 1 is provided, regardless of the case where each of the first member B and the second member B is constructed from two or more members to be position-fixed in an engaged state in each other or the case where it is constructed from a single member, if these members are prepared by adhesion, laser welding or press fitting, any of these members is prepared by casting, in the state that the abutment 2 is constructed by cast welding and position-fixing, the angular pipe concave portion 2b may be engaged in the side of the implant fixture 1 of the truncated conical portion 2a of the first member A.

Then, the male screw 3a of the abutment screw 3 is engaged in the female screw 1b of the implant fixture 1 while penetrating through the bolt hole 2e provided while penetrating from the inclined external surface of the gold cylinder external engagement portion 2d of the abutment 2 through the center of the truncated conical portion 2a; following the top portion of the abutment screw. The stopper portion 3b is then brought into contact with the end surface in the oral cavity side of the bolt hole 2e of the abutment 2, whereby the abutment 2 is connected and fixed to the implant fixture 1.

In this state, since the truncated conical portion 2a of the abutment 2 is formed so as to have a height positioned in the side of the implant fixture 1 as compared with the top portion in the oral cavity side of the gingiva, i.e., the height in which the truncated conical portion 2a is hindered by the gingiva of a patient, the truncated conical portion 2a is in a state that it is not seen.

Then, the gold cylinder 4 having the cast piece 6a of the dental prosthesis 6 comprised of the cast piece 6a having the porcelain 6b formed therein fixed in the external periphery of the cast piece anchorage 4b is engaged in the gold cylinder engagement portion 2d in such a state that in the inner portion of the cast piece anchorage portion 4b, the top portion of the abutment screw 3 is externally engaged and that the external engagement portion 4c of the cast piece anchorage portion 4b is engaged; and in the oral cavity side of the abutment 2, the plane 4a as the end surface in the side of the implant fixture 1 of the gold cylinder 4 is brought into contact with the external periphery side plane 2c provided in the upper external periphery in the oral cavity side of the truncated conical portion 2a as the base end portion of the gold cylinder external engagement portion 2d. At this time, if in the side of the implant fixture 1 of the gold cylinder external engagement portion 2d of the abutment 2, the angular pipe portion 2g is provided as well as in the side of implant fixture 1 of the space of the gold cylinder 4, the angular pipe concave portion 4g to be engaged in the above-described angular pipe portion 2g is provided, in case where the dental implant is used for a single tooth, the gold cylinder 4 can be accurately connected and fixed to the gold cylinder external engagement portion 2d of the abutment 2 without occurrence of any revolution.

Thereafter, if the gold screw 5 is screwed in the female screw 2f while penetrating through the hole 6c provided in the oral cavity side of the dental prosthesis 6 in the expanded portion of the center line of the cast piece anchorage 4b of the gold cylinder 4 as well as the dental prosthesis 6 is connected and fixed while supporting the top portion of the gold screw 5 by the projected portion 4e formed in the oral cavity side of the gold cylinder 4, and then, the above-described hole 6c provide in the oral cavity side of the dental prosthesis 6 is clogged by a dental cement or the like, the therapy of the dental implant is completed.

In the light of the above, the angled dental implant according to the present invention is free from the defects of, as the conventional dental prosthetic treatment of the deficit tooth portion, a method for using a bridge or a method for using a denture base, that is, in the former method, since healthy natural teeth in the both sides of the deficit tooth portion are cut, or an occlusion pressure is not directly applied to the dental prosthesis part positioned in the deficit tooth portion, a bone loss is likely caused in the instant side; and in the latter method, a sense of incongruity is generated during the use of the dental prosthesis, the dental base covers receptors lying scattered in the oral mucosa tissue, thereby generating blunting of the taste, and/or a loss of the residual ridge is caused during the use for a long period of time. In the dental implant to be used in an excellent therapeutic method making it possible to prepare dental prostheses having a suitable state from the standpoints of the knowledge of the dental anatomy, as in the anterior tooth portion in the maxilla, the abutment is connected and fixed by means of the abutment screw while inclining the center line of the gold cylinder external engagement portion against the center axis of the implant fixture, and the gold cylinder functioning as a fixing device of the dental prosthesis is connected and fixed in the oral cavity side of the abutment by means of the gold screw. In this case, the oral cavity side of the abutment or the end portion in the implant fixture side of the gold cylinder is projected from the gingiva so that the esthetics are remarkably impaired, leading to the hindrance of spread of dental implants. In order to overcome this defect, the truncated conical portion of the abutment having in the oral cavity side the external periphery side plane functioning as a support surface for supporting the end surface in the implant fixture side of the gold cylinder in which the cast piece of the dental prosthesis is fixed to the surrounding of the cast piece anchorage thereof is a plane perpendicular against the axis of the truncated conical portion and is formed so as to have a height positioned in the side of the implant fixture as compared with the top portion in the oral cavity side of the gingiva of a patient, i.e., a height such that the truncated conical portion is hidden by the gingiva of the patient. Therefore, in a state that the therapy of the dental implant has been completed, the truncated conical portion is not seen. The gold cylinder in which the plane of the end surface in the side of the implant fixture comes into contact with the external periphery side plane of the abutment has an external shape in which the diameter in the oral cavity side is reduced as compared with that in the plane and form the cast piece anchorage whose center line is coincident with the center line of the gold cylinder external engagement portion of the abutment inclined against the center axis of the implant fixture. Accordingly, even if a collar portion with a thin thickness forming a step portion in the oral cavity side is not provided in the side of the implant fixture of the gold cylinder, in the dental prosthesis fixed to the cast piece anchorage of the gold cylinder, the external surface of the end portion in the side of the implant fixture is hidden by the gingiva of the patient, or is positioned in a level substantially the same as that in the top portion of the gingiva of the patient, thereby generating the state that the abutment or the end portion in the side of the implant fixture of the gold cylinder is exposed. Thus, the defect that the esthetics are impaired is dissolved.

In addition, if an angular pipe portion is provided in the side of the implant fixture of the gold cylinder external engagement portion of the abutment, and an angular pipe concave portion to be engaged in the foregoing angular pipe portion is provided in the side of the implant fixture in the space of the gold cylinder, in case where the dental implant is used for a single tooth, the gold cylinder can be accurately connected and fixed to the gold cylinder external engagement portion of the abutment without occurrence of any revolution.

In addition, if the abutment comprises a construction comprising a first member comprising the truncated conical portion in which in the oral cavity side, a groove concaved in the side of the implant fixture and/or a projection projected in the oral cavity side are formed in the inside of the external periphery side plane; and a second member in which in the side of the implant fixture, a convex to be internally engaged in the groove and/or a convex to be externally engaged in the projection are provided, the position is fixed in a state that the groove and convex and/or the projection and concave are engaged in each other, and in a portion positioned in the oral cavity side, the gold cylinder external engagement portion whose center line is inclined against the center axis of the implant fixture, not only the construction can be made from members of a linear symmetry or an approximately linear symmetry against the respective center lines, so that its preparation is easy, but also in particular, the external periphery surface of the truncated conical portion of the first member functioning as a portion coming into contact with a gingiva can be mechanically processed so as to have a fine plane roughness, whereby the sealability by the gingiva is improved to prevent bacteria from retention.

Also, if a collar portion partitioning a base end portion of a dental prosthesis, which is formed in a thin thickness in the side of the implant fixture and has a step portion in the oral cavity side, is provided, the position of the base end portion to be fixed to the external periphery of the gold cylinder can be made accurate, and the appearance can be further improved.

The angled dental implant having such carious effects according to the present invention greatly contributes to the dental field and is very valuable.

While the invention has been described in detail and with reference to specific embodiments thereof, it will be apparent to one skilled in the art that various changes and modifications can be made therein without departing from the spirit and scope thereof.

What is claimed is:

1. An angled dental implant comprising:

an implant fixture to be implanted in and fixed to an implantation hole formed in a mandible, said fixture having a columnar portion with an angular pipe portion on an oral cavity end of said columnar portion, said fixture including a threaded female bolt hole;

an abutment having a truncated conical portion, said abutment having a concave angular pipe portion, at a narrow end of said conical portion, configured to engage said angular pipe portion of said fixture, said end portion having an outer diameter substantially equal to an outer diameter of said columnar portion of said fixture, said abutment including a cylinder engagement portion with a center line which is configured to be inclined relative to a center axis of said fixture, said abutment including a peripheral face with lies in a plane to be substantially perpendicular to the center axis of said fixture, said abutment including a bolt hole configured to be longitudinally aligned with the center axis of said fixture wherein said bolt hole extends through said cylinder engagement portion, wherein said abutment is to be anchored to said female threaded bolt hole of said fixture with an abutment screw passing through said bolt hole; and a cylinder configured to engage said cylinder engagement portion, said cylinder having an abutment end with a face configured to cooperate with said peripheral face of said abutment, said cylinder having an oral cavity end which is smaller in diameter than said abutment end, said cylinder including a cast piece anchorage portion with a center line arranged to substantially coincide with the center line of said engagement portion of said abutment, said cylinder to be anchored to said engagement portion of said abutment with a screw passing through a bolt hole formed in said oral cavity end of said cylinder.

2. An angled dental implant as claimed in claim 1, wherein a convex angular pipe portion is provided at a wide end of said conical portion of said abutment, a concave angular pipe portion is provided on said cylinder which is configured to be engaged with said convex angular pipe portion on said wide end of said conical portion.

3. An angled dental implant as claimed in claim 7, wherein said abutment comprises:

a first member forming the truncated conical portion, said first member including a groove formed inward from the peripheral face; and a second member forming said cylinder engagement portion, said second member including a projection configured to engage the groove formed on the first member.

4. An angled dental implant as claimed in claim 3, wherein said cylinder includes a collar portion formed adjacent said abutment end of said cylinder, said collar including a step facing substantially towards said oral cavity end of said cylinder.

5. An angled dental implant as claimed in claim 2, wherein said abutment comprises:

a first member forming the truncated conical portion, said first member including a projection formed inward from the peripheral face; and a second member forming said cylinder engagement portion, said second member including a groove configured to engage the projection formed on the first member.

6. An angled dental implant as claimed in claim 5, wherein said cylinder includes a collar portion formed adjacent said abutment end of said cylinder, said collar including a step facing substantially towards said oral cavity end of said cylinder.

7. An angled dental implant as claimed in claim 2, wherein said cylinder includes a collar portion formed adjacent said abutment end of said cylinder, said collar including a step facing substantially towards said oral cavity end of said cylinder.

8. An angled dental implant as claimed in claim 1, wherein said abutment comprises:

a first member forming the truncated conical portion, said first member including a groove formed inward from the peripheral face; and a second member forming said cylinder engagement portion, said second member including a projection configured to engage the groove formed on the first member.

9. An angled dental implant as claimed in claim 8, wherein said cylinder includes a collar portion formed adjacent said abutment end of said cylinder, said collar including a step facing substantially towards said oral cavity end of said cylinder.

10. An angled dental implant as claimed in claim 1, wherein said abutment comprises:

a first member forming the truncated conical portion, said first member including a projection formed inward from the peripheral face; and a second member forming said cylinder engagement portion, said second member including a groove configured to engage the projection formed on the first member.

11. An angled dental implant as claimed in claim 10, wherein said cylinder includes a collar portion formed adjacent said abutment end of said cylinder, said collar including a step facing substantially towards said oral cavity end of said cylinder.

12. An angled dental implant as claimed in claim 1, wherein said cylinder includes a collar portion formed adjacent said abutment end of said cylinder, said collar including a step facing substantially towards said oral cavity end of said cylinder.

* * * * *